(12) United States Patent
Long

(10) Patent No.: US 8,591,596 B2
(45) Date of Patent: Nov. 26, 2013

(54) SEMI-CONSTRAINED ANKLE PROSTHESIS HAVING A ROTATING BEARING INSERT

(75) Inventor: Jack F. Long, Warsaw, IN (US)

(73) Assignee: DePuy Synthes Products, LLC, Raynham, MA (US)

(*) Notice: Subject to any disclaimer, the term of this patent is extended or adjusted under 35 U.S.C. 154(b) by 0 days.

(21) Appl. No.: 12/789,602

(22) Filed: May 28, 2010

(65) Prior Publication Data
US 2011/0295380 A1 Dec. 1, 2011

(51) Int. Cl.
*A61F 2/42* (2006.01)
(52) U.S. Cl.
USPC ........................................ 623/21.18
(58) Field of Classification Search
USPC .......... 623/20.14, 20.15, 20.21, 20.22, 20.26, 623/20.27, 20.28, 20.29, 20.3, 20.31, 20.32, 623/20.33, 21.11, 21.12, 21.17, 21.18, 623/23.39, 23.4, 23.41
See application file for complete search history.

(56) References Cited

U.S. PATENT DOCUMENTS

| 4,470,158 | A | | 9/1984 | Pappas et al. | |
|---|---|---|---|---|---|
| 4,963,152 | A | * | 10/1990 | Hofmann et al. | 623/20.31 |
| 6,053,945 | A | * | 4/2000 | O'Neil et al. | 623/20.32 |
| 6,126,692 | A | * | 10/2000 | Robie et al. | 623/20.32 |
| 6,379,388 | B1 | * | 4/2002 | Ensign et al. | 623/20.34 |
| 6,969,407 | B2 | * | 11/2005 | Klotz et al. | 623/21.12 |
| 7,011,687 | B2 | | 3/2006 | Deffenbaugh et al. | |
| 7,323,012 | B1 | | 1/2008 | Stone et al. | |
| 2004/0143336 | A1 | * | 7/2004 | Burkinshaw | 623/20.15 |
| 2006/0142870 | A1 | | 6/2006 | Robinson et al. | |
| 2008/0228281 | A1 | * | 9/2008 | Forrer et al. | 623/19.12 |
| 2008/0306605 | A1 | | 12/2008 | Hasselman | |

OTHER PUBLICATIONS

PCT International Search Report, Jul. 18, 2011.
Australian Patent Examination Report No. 1, Australian Patent Application No. 2011258292, Sep. 9, 2013, 3 pages.

* cited by examiner

*Primary Examiner* — David Isabella
*Assistant Examiner* — Marcia Hoffman
(74) *Attorney, Agent, or Firm* — Barnes & Thornburg LLP

(57) ABSTRACT

A semi-constrained ankle prosthesis includes a tibial component configured to be coupled to a surgically-prepared surface of the distal end of a tibia, and a bearing insert locked to the tibial component. The bearing insert is rotative relative to the tibial component and has an articular surface formed in an inferior surface thereof.

12 Claims, 11 Drawing Sheets

SEMI-CONSTRAINED ANKLE PROSTHESIS HAVING A ROTATING BEARING INSERT

TECHNICAL FIELD

The present disclosure relates generally to an implantable orthopaedic prosthesis, and more particularly to an implantable ankle prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of an ankle replacement procedure, a tibial component is implanted into the patient's tibia, and a talar component is implanted into a patient's talus. A polymer bearing insert is positioned between the tibial component and the talar component. The articular surface of the talar component bears against the articular surface of the bearing insert.

Depending on the condition of the patient's soft tissue, either an unconstrained ankle prostheses or a semi-constrained ankle prosthesis may be implanted. For example, if the patient's ankle ligaments are relatively intact, an unconstrained ankle prosthesis may be used. An unconstrained ankle prostheses has two articulating interfaces thereby creating desirable degrees of freedom. One articulating interface is between the tibial component and the bearing insert, with the other being between the bearing insert and the talar component. In the absence of sufficient soft tissue, a semi-constrained ankle prosthesis is used. Such an implant includes only one articulating interface—the interface between the bearing insert and the talar component. Unlike unconstrained implants, the polymer bearing insert is locked in position relative to the tibia component in a semi-constrained ankle prosthesis.

SUMMARY

According to one aspect, a semi-constrained ankle prosthesis includes a talar component configured to be coupled to a surgically-prepared surface of the proximal end of a talus. The talar component has an articular surface. The ankle prosthesis also includes a tibial component configured to be coupled to a surgically-prepared surface of the distal end of a tibia. The tibial component includes a platform having a recess formed therein. A bearing insert includes a base having an articular surface formed in an inferior surface thereof. The articular surface of the bearing insert is configured to articulate with the articular surface of the talar component. The bearing insert also has a pedestal extending superiorly from a superior surface of the base. The pedestal is positioned in the recess of the tibial component so as to lock the bearing insert to the base and permit the bearing insert to rotate relative to the base.

The platform of the tibial component includes an annular sidewall that defines the recess. The annular sidewall may have an undercut formed therein. The pedestal of the bearing insert may include a retaining flange that is positioned in the undercut. The pedestal of the bearing insert may also include a locking tab positioned in the undercut.

The retaining flange may be located on the posterior side of the pedestal, with the locking tab being located on the anterior side of the pedestal.

An anterior sidewall extends from a superior surface of the platform to the an inferior surface of the platform. The anterior sidewall may have an opening formed therein that opens into the recess. The locking tab of the bearing insert is wider than the opening formed in the anterior sidewall of platform.

The platform of the tibial component includes an inferior surface positioned in contact with the superior surface of the bearing insert, and a bottom surface that is parallel to, and spaced apart superiorly from, the inferior surface. The bottom surface defines the bottom of the recess. Both the inferior surface and the bottom surface may be embodied as polished metal surfaces.

According to another aspect, a semi-constrained ankle prosthesis includes a tibial component configured to be coupled to a surgically-prepared surface of the distal end of a tibia, and a polymeric bearing insert. The bearing insert has an articular surface formed in an inferior surface thereof. The bearing insert is locked to the tibial component and rotative relative thereto.

The ankle prosthesis may also include a talar component configured to be coupled to a surgically-prepared surface of the proximal end of a talus. The talar component has an articular surface that is configured to articulate with the articular surface of the tibial component.

The tibial component may include an annular sidewall that defines a recess, with the bearing insert having a superiorly extending pedestal that is positioned in the recess.

The annular sidewall may have an undercut formed therein, with the pedestal having a retaining flange positioned in the undercut. The pedestal may also include a locking tab positioned in the undercut.

The retaining flange may be located on the posterior side of the pedestal, with the locking tab being located on the anterior side of the pedestal.

An anterior sidewall extends from a superior surface of the tibial component to the an inferior surface of the platform. The anterior sidewall may have an opening formed therein that opens into the recess. The locking tab of the bearing insert is wider than the opening formed in the anterior sidewall of platform.

The tibial component may include a polished metal inferior surface positioned in contact with a superior surface of the bearing insert.

According to another aspect, a semi-constrained ankle prosthesis includes a tibial component configured to be coupled to a surgically-prepared surface of the distal end of a tibia, and a bearing insert snapped-locked to the tibial component. The bearing insert is rotative relative to the tibial component and has an articular surface formed in an inferior surface thereof.

The ankle prosthesis may also include a talar component configured to be coupled to a surgically-prepared surface of the proximal end of a talus. The talar component has an articular surface that is configured to articulate with the articular surface of the tibial component.

The tibial component may be metallic, with the bearing insert being polymeric.

The tibial component may include an annular sidewall that defines a recess, with the bearing insert having a superiorly extending pedestal that is positioned in the recess.

The annular sidewall may have an undercut formed therein, with the pedestal having a retaining flange positioned in the undercut. The pedestal may also include a locking tab positioned in the undercut.

The retaining flange may be located on the posterior side of the pedestal, with the locking tab being located on the anterior side of the pedestal.

An anterior sidewall extends from a superior surface of the tibial component to the an inferior surface of the platform. The anterior sidewall may have an opening formed therein that opens into the recess. The locking tab of the bearing insert is wider than the opening formed in the anterior sidewall of platform.

The tibial component may include a polished metal inferior surface positioned in contact with a superior surface of the bearing insert.

BRIEF DESCRIPTION OF THE DRAWINGS

The detailed description particularly refers to the following figures, in which.

DETAILED DESCRIPTION OF THE DRAWINGS

Figure 1:
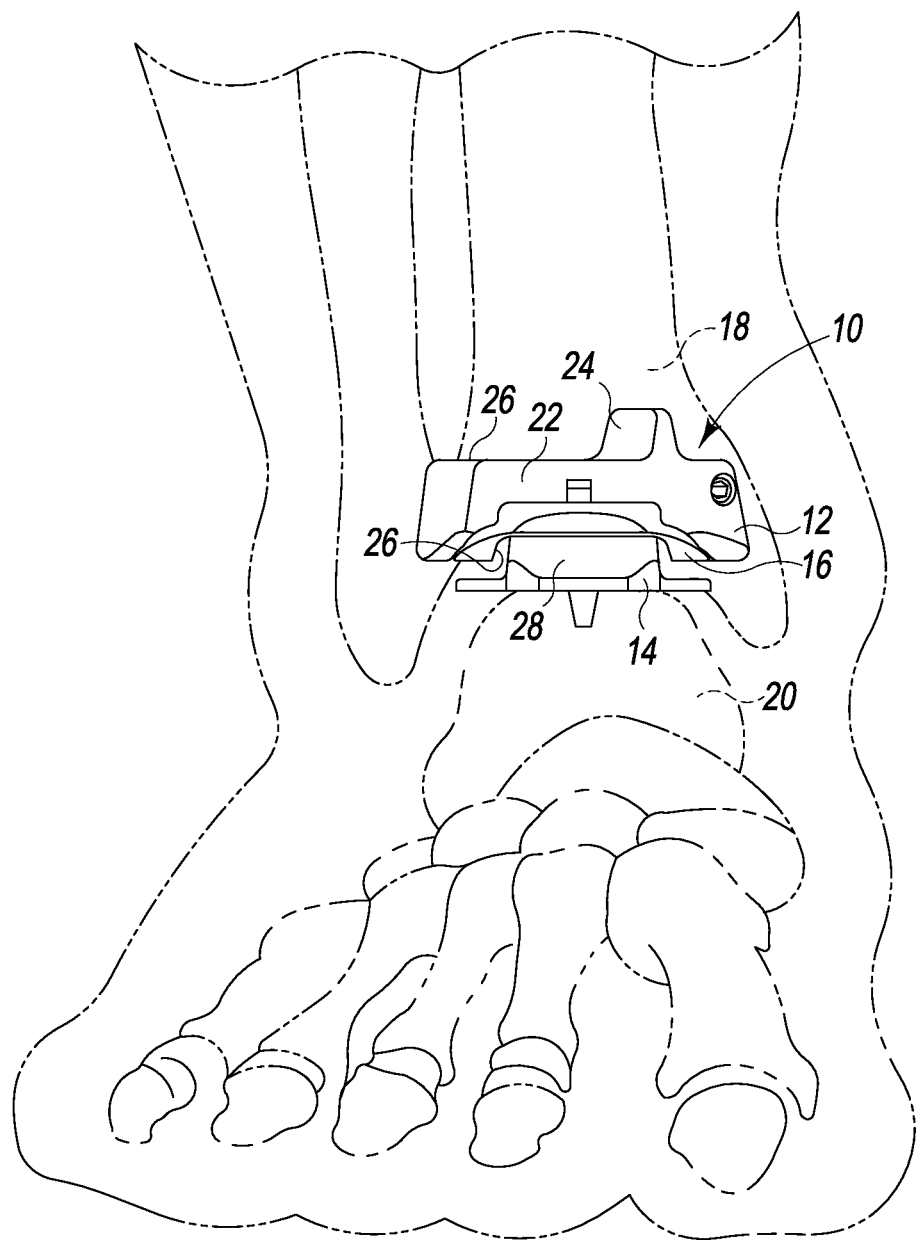
FIG. 1 is a diagrammatic view showing a semi-constrained rotating ankle prosthesis implanted into the ankle of a patient.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-7, there is shown a semi-constrained ankle prosthesis 10. The ankle prosthesis 10 includes a tibial component 12, a talar component 14, and a bearing insert 16. The tibial component 12 is configured to be implanted into a surgically-prepared surface of the distal end of a patient's tibia 18, whereas the talar component 14 is configured to be implanted into a surgically-prepared surface of the proximal end of a patient's talus 20. In such a way, the ankle prosthesis 10 allows for flexion, extension, and rotation in a manner that mimics that of a natural ankle.

The tibial component 12 includes a platform 22 having a fixation member, such as a keel 24, extending superiorly away from its superior surface 26. The keel 24 is configured to be implanted into a slot (not shown) formed in the surgically prepared distal end of a patient's tibia 18. It should be appreciated that other fixation members, such as one or more fins, stems, pegs, or posts may be used in lieu of the keel 24.

The bearing insert 16 is locked to the tibial component 12. What is meant herein by the term "locked" is that the bearing insert is fastened to the tibial component in a manner that resists linear movement of the bearing insert relative to the tibial component in the anterior/posterior, medial/lateral, and superior/inferior directions. For instance, when the bearing insert is "locked" to the tibial component, the bearing insert is prevented from lifting off, or otherwise being unfastened from, the tibial component in the absence of manipulation to do so from a surgeon or other user. In the exemplary embodiment described herein, the bearing insert 16 is snap-locked to the tibial component 16. The term "snapped-locked" means that the bearing insert is fastened to the tibial component automatically when the bearing insert is pushed into position with the tibial component. For example, as will be discussed below in greater detail, the bearing insert 16 includes a locking tab that snaps into an undercut formed in the tibial component 12 thereby locking the insert 16 to the tibial component 12.

As shown in FIG. 1, the bearing insert 16 includes a concave articular surface 26 that is configured to articulate with a convex articular surface 28 of the talar component 14. Specifically, the articular surface 26 of the bearing insert 16 is configured to emulate the configuration of the patient's natural tibial articular surfaces when the tibial component 12 is implanted into the surgically-prepared distal end of the patient's tibia 18, whereas the articular surface 28 of the talar component 14 mimics the patient's natural talar articular surfaces when the talar component 14 is implanted into the surgically-prepared proximal end of the patient's talus 20. As such, articulation between the articular surface 28 of the talar component 14 and the articular surface 26 of the bearing insert 16 mimics articulation of the patient's natural ankle.

Figure 2:
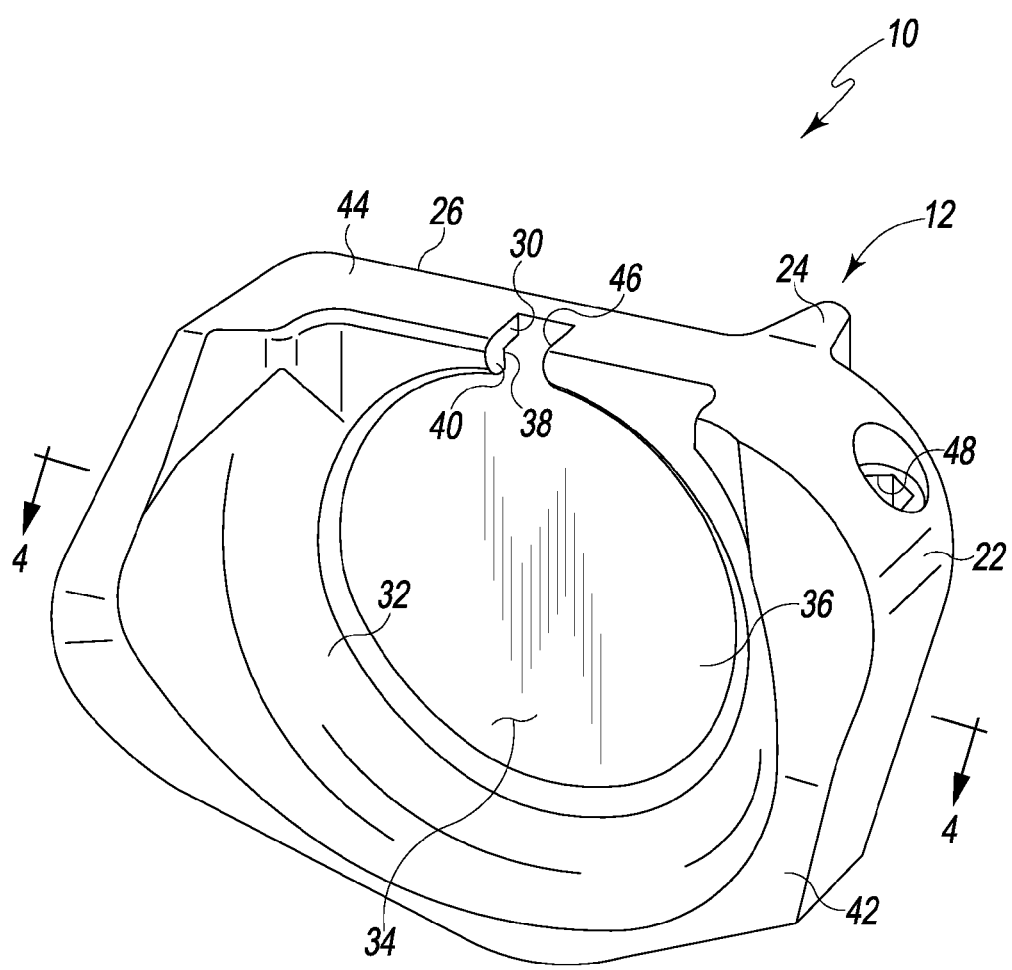
FIG. 2 is a perspective view of the tibial component of the semi-constrained rotating ankle prosthesis of FIG. 1.
Figure 3:
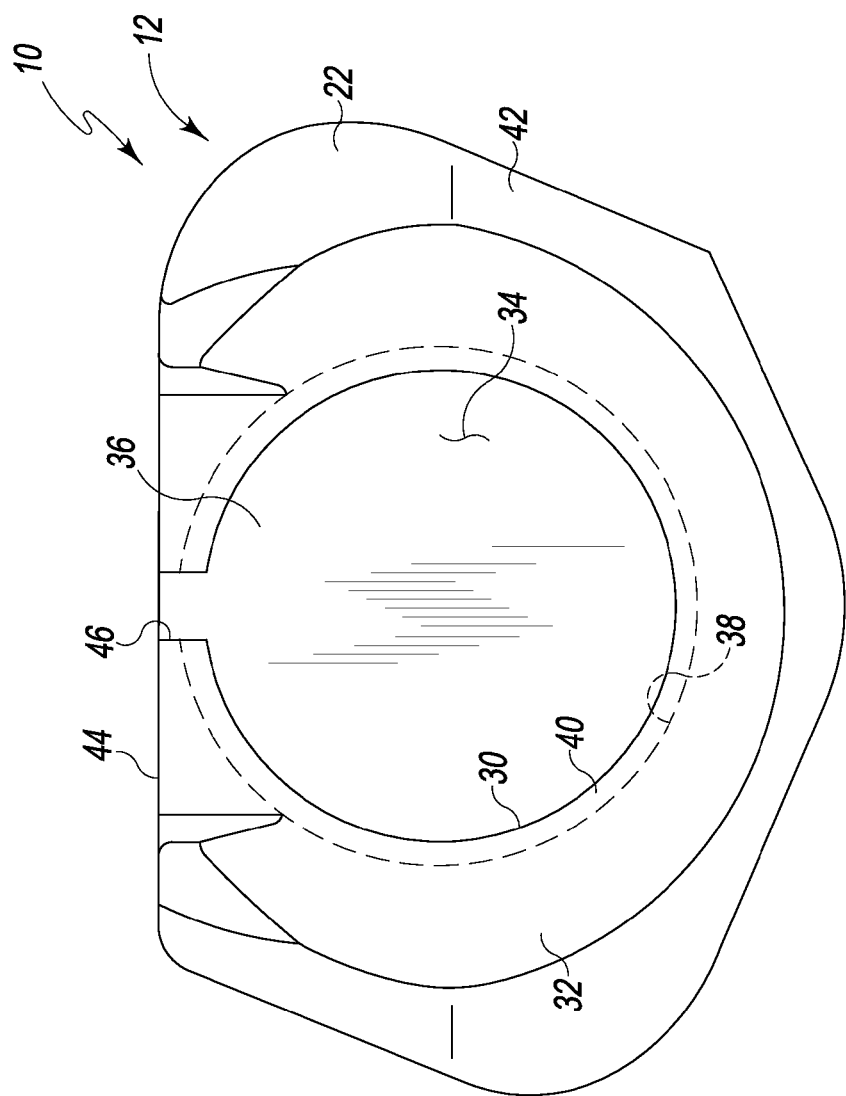
FIG. 3 is an inferior plan view of the tibial component of FIG. 2.
Figure 4:
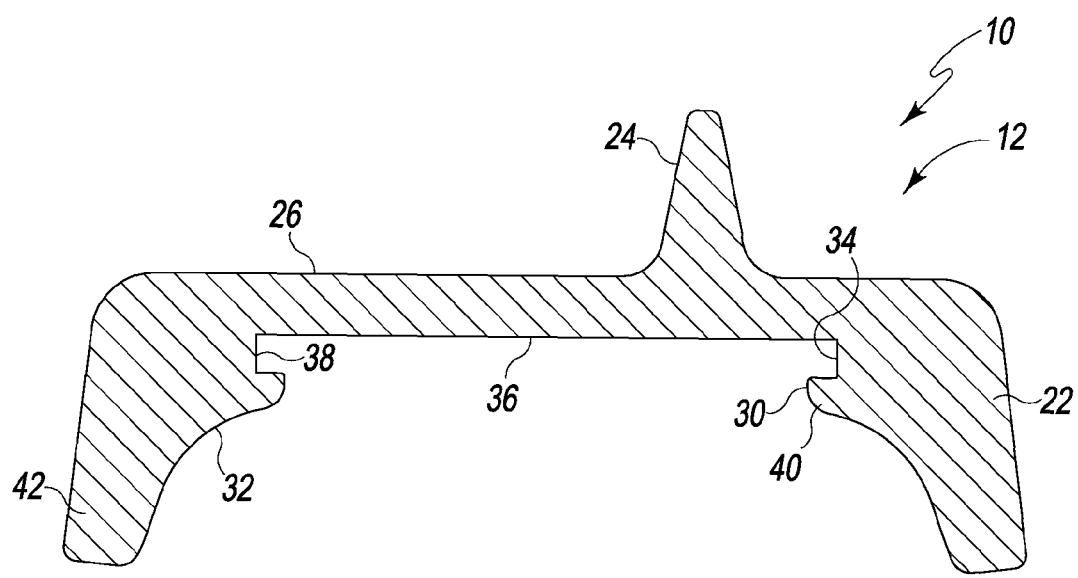
FIG. 4 is a cross-sectional view of the tibial component taken along the line 4-4 of FIG. 2, as viewed in the direction of the arrows.

As shown in FIGS. 2-4, the platform 22 has an annular sidewall 30 extending superiorly from of its inferior surface 32. As will be discussed below in greater detail, the annular sidewall 30 defines a recess 34 into which the bearing insert's pedestal is received. The recess 34 is a blind recess being defined superiorly by a bottom surface 36. The bottom surface 36 is parallel to, and spaced apart superiorly from, the inferior surface 32 of the tibial component's platform 22. The annular sidewall 30 of the tibial component's platform 22 has an undercut 38 formed therein. As can be seen in phantom lines in FIG. 3, the undercut 38 extends around the periphery of the recess 34. An annular lip 40 defines the inferior surface of the undercut 36, whereas the bottom surface 36 of the recess 34 defines its superior surface.

Figure 9:
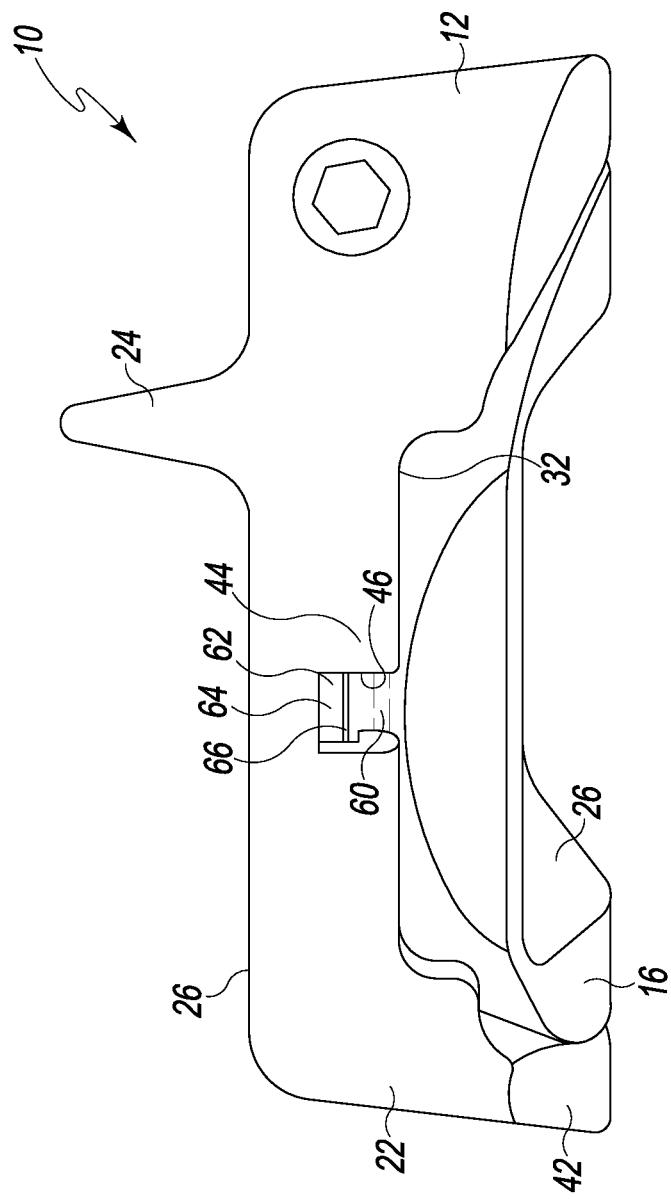
FIG. 9 is an anterior view showing the bearing insert locked to the tibial component.

An outer sidewall 42 extends inferiorly from the inferior surface 32 of the tibal component's platform 22. As can be seen in FIG. 9, the bearing insert 16 is nested within the sidewall 42. The sidewall 42 includes an inner surface that conforms to the outer surface of the bearing insert 16. In such a way, the inner surface of the tibial component's sidewall 42 functions as a guide during rotation of the bearing insert 16 relative to the tibial component 12.

In the exemplary embodiment described herein, the recess 34 of the tibial component 12 is not closed, but rather is open along a portion of its anterior side. In particular, as can be seen in FIGS. 2 and 9, the tibial component's platform 22 has an anterior sidewall 44 that extends from its superior surface 26 to its inferior surface 32. An opening such as a slot 46 is formed in the anterior sidewall 44. As can be seen in FIG. 3, the slot 46 opens into the platform's recess 34. That is, the slot 46 is open to both the outer surface of the anterior sidewall 44 and the annular sidewall 30 of the recess 34. As will be discussed below in greater detail, the slot 46 permits access to the locking mechanism of the bearing insert 16 so as to allow the bearing insert 16 to be unlocked and thereafter removed from the tibial component 12 by a surgeon or other user.

Figure 11:
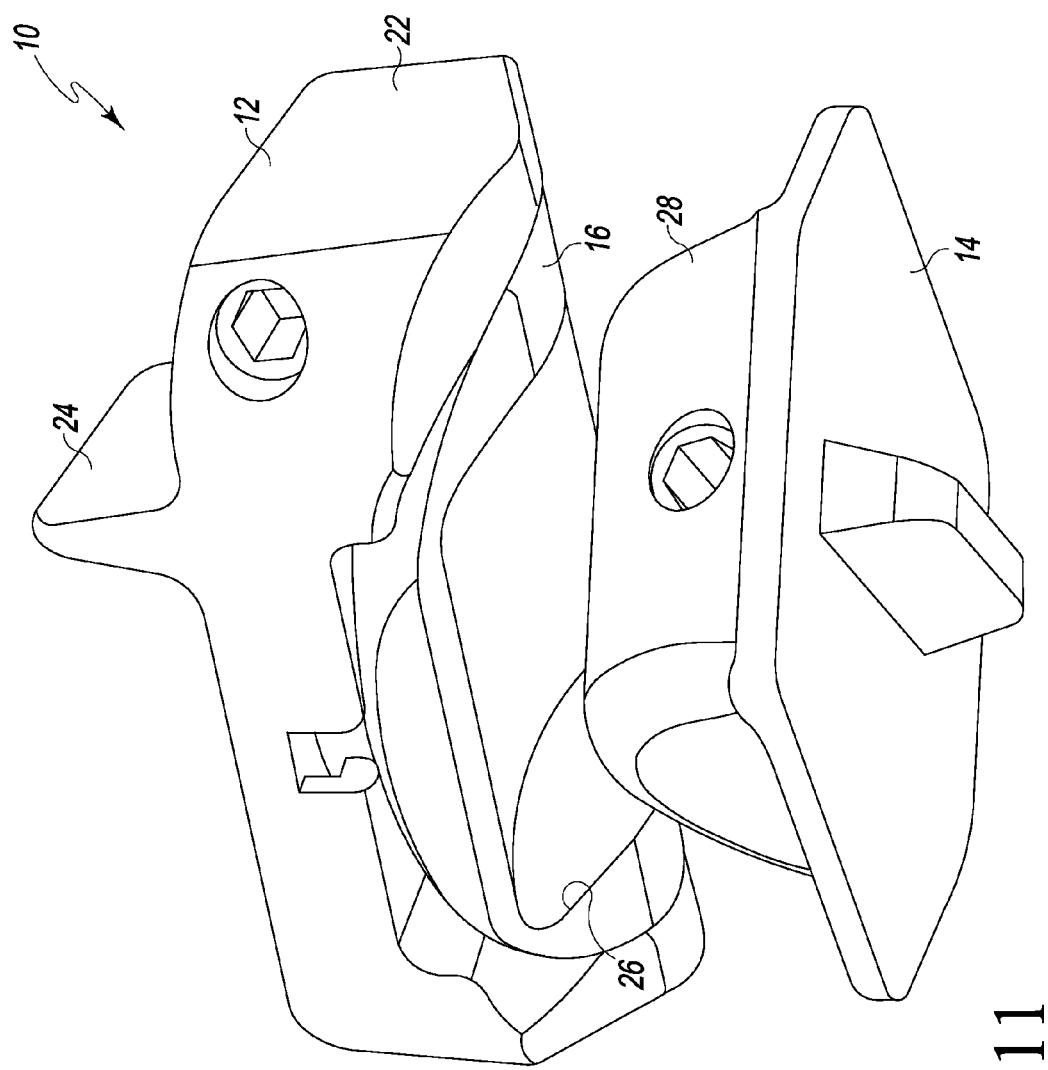
FIG. 11 is a perspective view showing the talar component misaligned with the bearing insert and tibial component.
Figure 12:
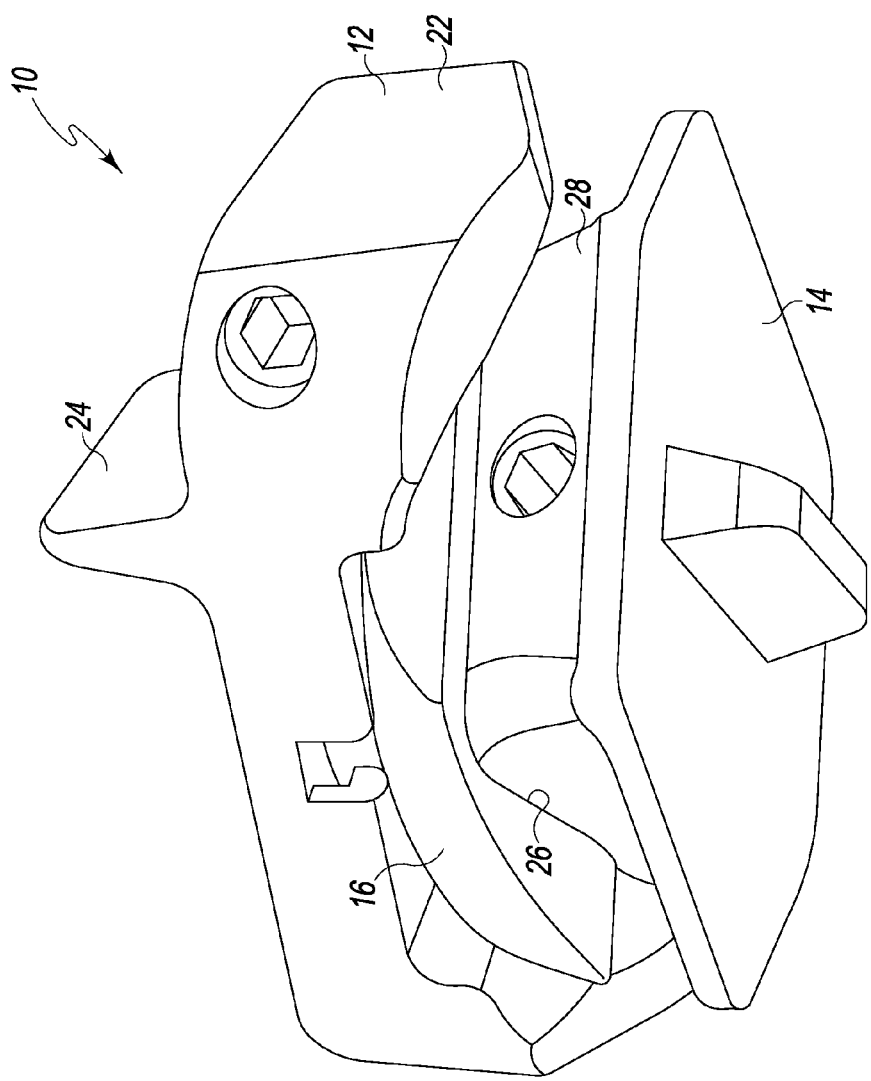
FIG. 12 is a perspective view showing the bearing insert having been rotated to accommodate the misaligned talar component.

The anterior sidewall 44 also has a hex-shaped hole 48 formed therein (see FIG. 2). A surgeon may position a hex-shaped tip of a surgical instrument (not shown) in the hex-shaped hole 48 to facilitate implantation of the tibial component 12. Once implanted, the instrument is removed from the hole 48. As can be seen in FIGS. 11 and 12, the talar component 14 has a similar hex-shaped hole to facilitate implantation of the talar component 14 in a similar manner.

Figure 7:
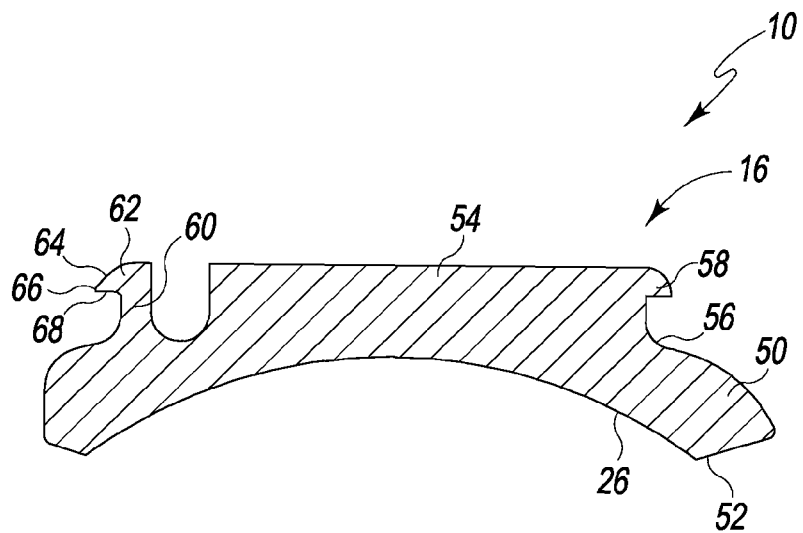
FIG. 7 is a cross-sectional view of the bearing insert taken along the line 7-7 of FIG. 5, as viewed in the direction of the arrows.
Figure 5:
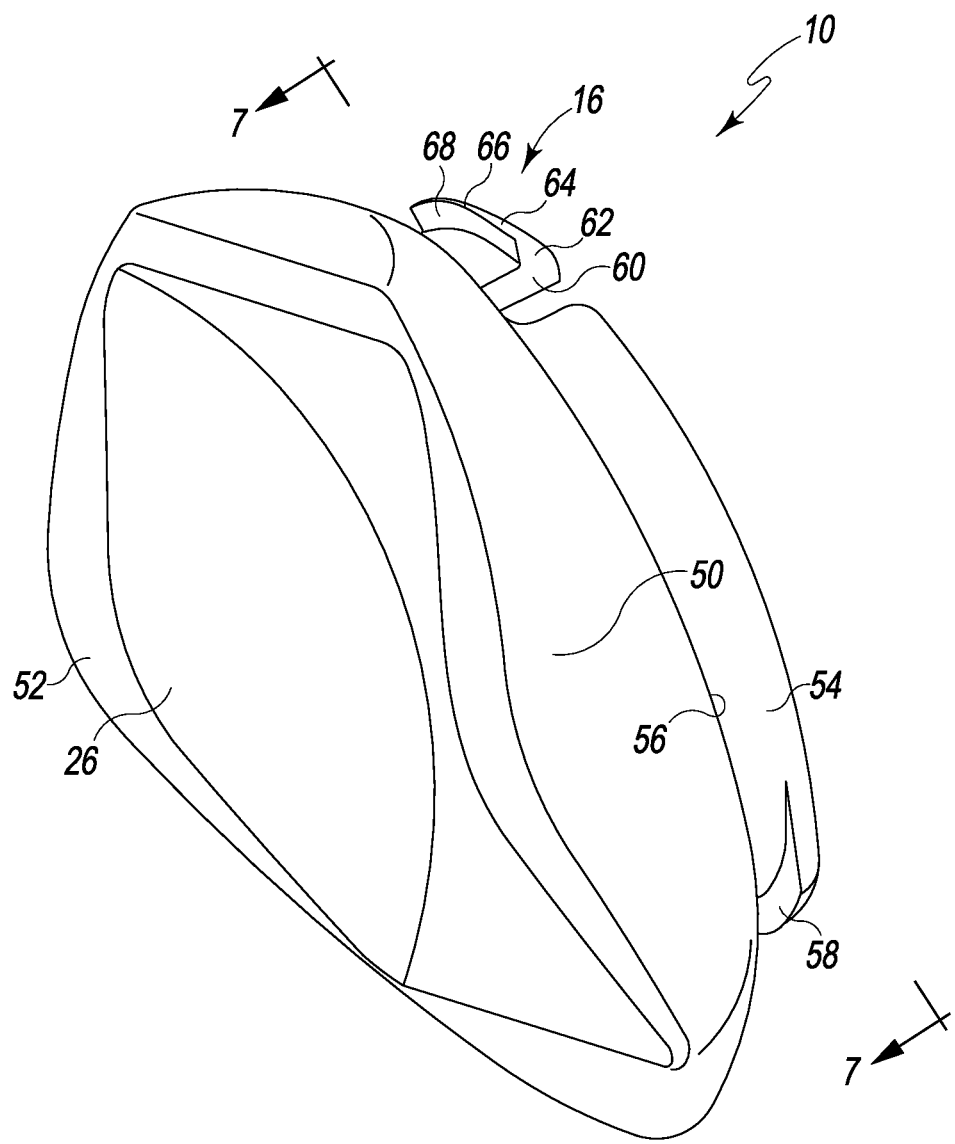
FIG. 5 is a perspective view of the bearing insert of the semi-constrained rotating ankle prosthesis of FIG. 1.
Figure 6:
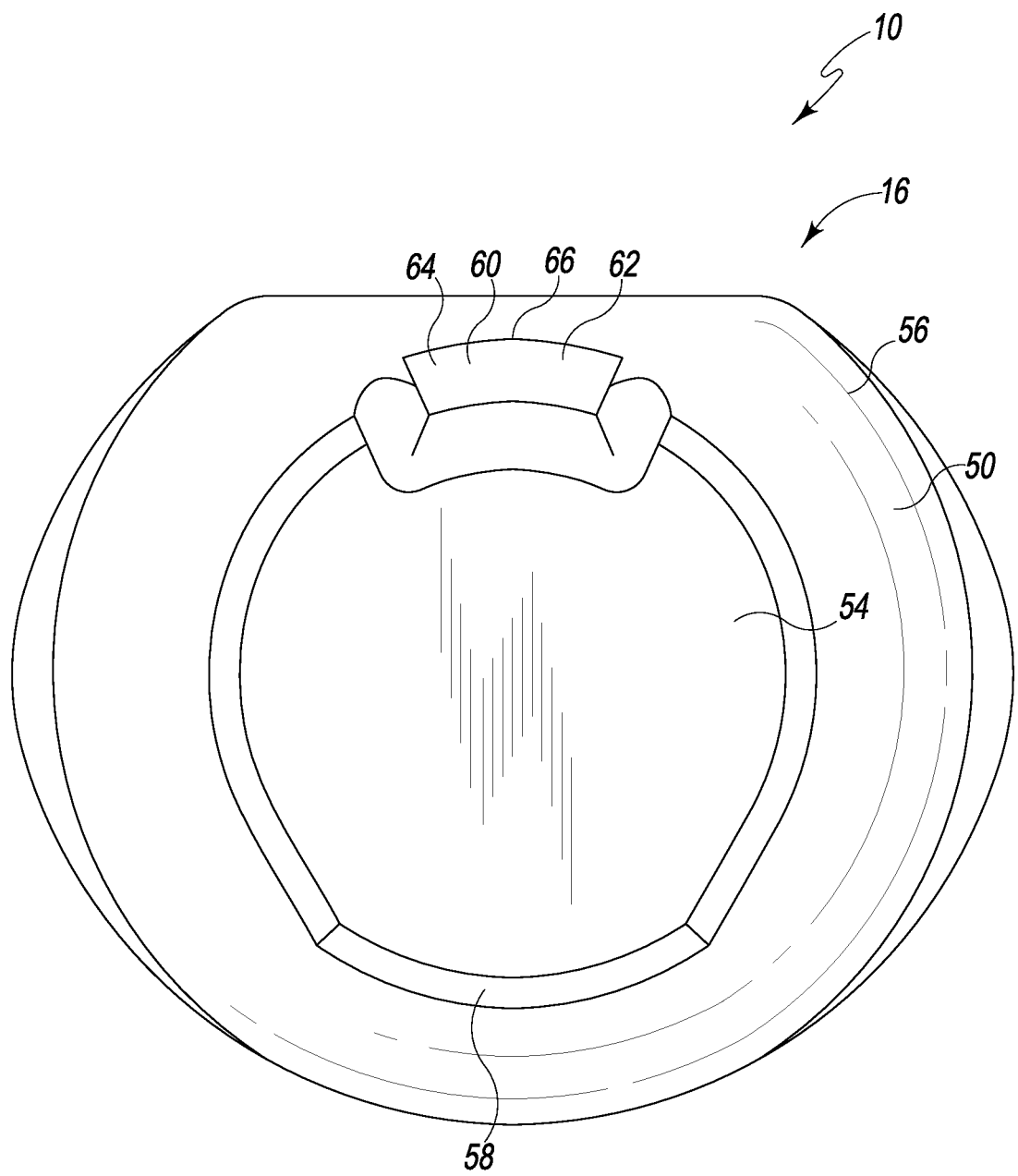
FIG. 6 is a superior plan view of the bearing insert of FIG. 5.

As shown in FIGS. 5-7, the concave articular surface 26 of the bearing insert 16 is defined in the inferior surface 52 of its base 50. A pedestal 54 extends superiorly away from the superior surface 56 of the base 50. As can be seen best in FIG. 6, the superior end of the pedestal 54 has a retaining flange 58 that extends posteriorly away from the center of the pedestal 54. The retaining flange 58 is generally arcuate in shape and extends along a portion of the posterior side of the pedestal 54. Opposite the retaining flange 54, the pedestal 54 has a locking tab 60 on its anterior side. The locking tab 60 is cantilevered to the superior surface 56 of the base 50. As such, the locking tab 60 may be deflected or otherwise urged posteriorly from the position shown in FIGS. 6 and 7 during insertion of the pedestal 54 into a first position in the recess 34 of the tibial component 12.

Figure 8:
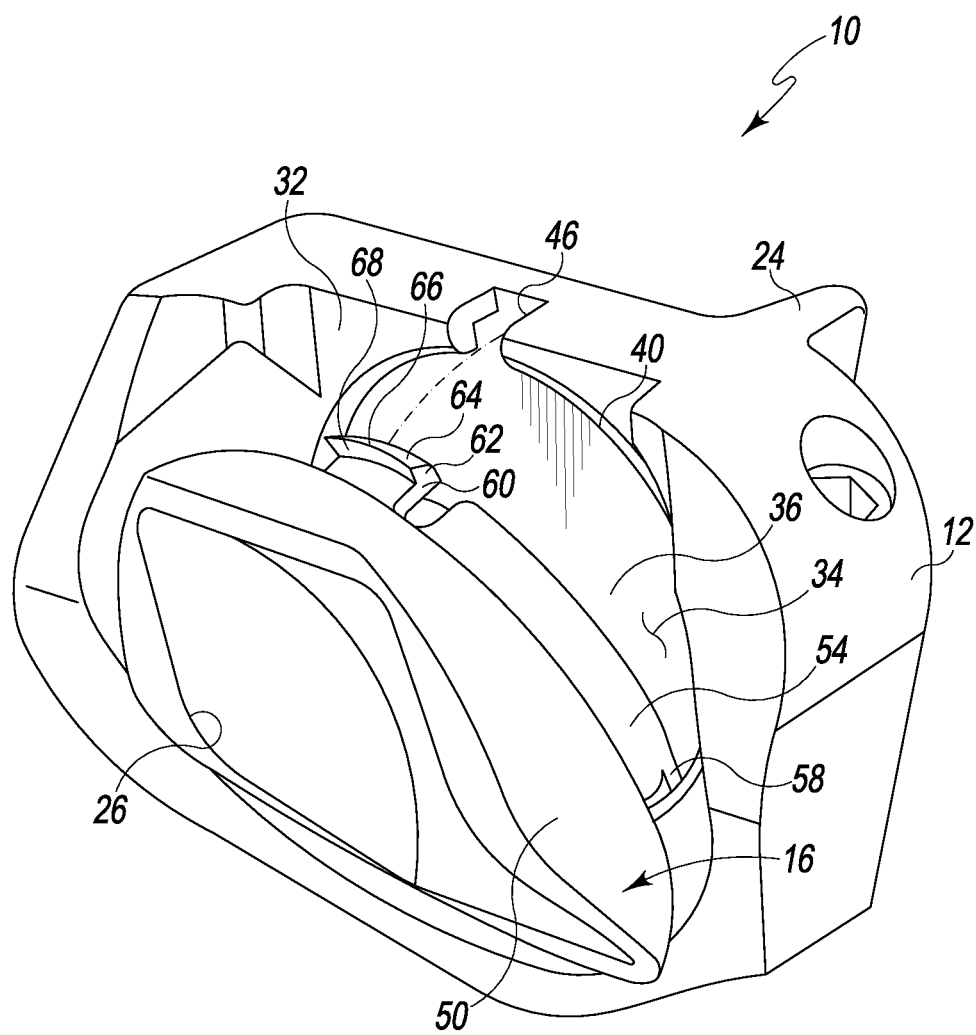
FIG. 8 is a perspective view showing the bearing insert being snap-locked into the tibial component.

The retaining flange 58 and locking tab 60 of the pedestal 54 facilitate locking the bearing insert 16 to the tibial component 12. In particular, as shown in FIG. 8, the posterior end of the pedestal 54 may be tilted toward the posterior portion of the tibial component's recess 30 such that the retaining flange 58 is advanced toward the undercut 38. Once the retaining flange 58 is positioned under the annular lip 40 formed by the undercut 38, the anterior side of the pedestal 54 may then be moved superiorly toward the anterior portion of the tibial component's recess 30 (i.e., along the path shown by the phantom line of FIG. 8). The distal end 62 of the locking tab 60 has an angled surface 64 defined therein. The angled surface 64 functions as a cam surface that causes the distal end 62 of the locking tab 60 to be urged posteriorly when it engages the inferior surface 32 of the tibial component's platform 22. Once the anterior edge 66 of the angled surface 64 clears the inferior surface 32 of the tibial component's platform 22, the locking tab 60 snaps or otherwise moves anteriorly such that the inferior edge 68 of its distal end 62 is captured in the undercut 38 by the undercut's annular lip 40.

Figure 10:
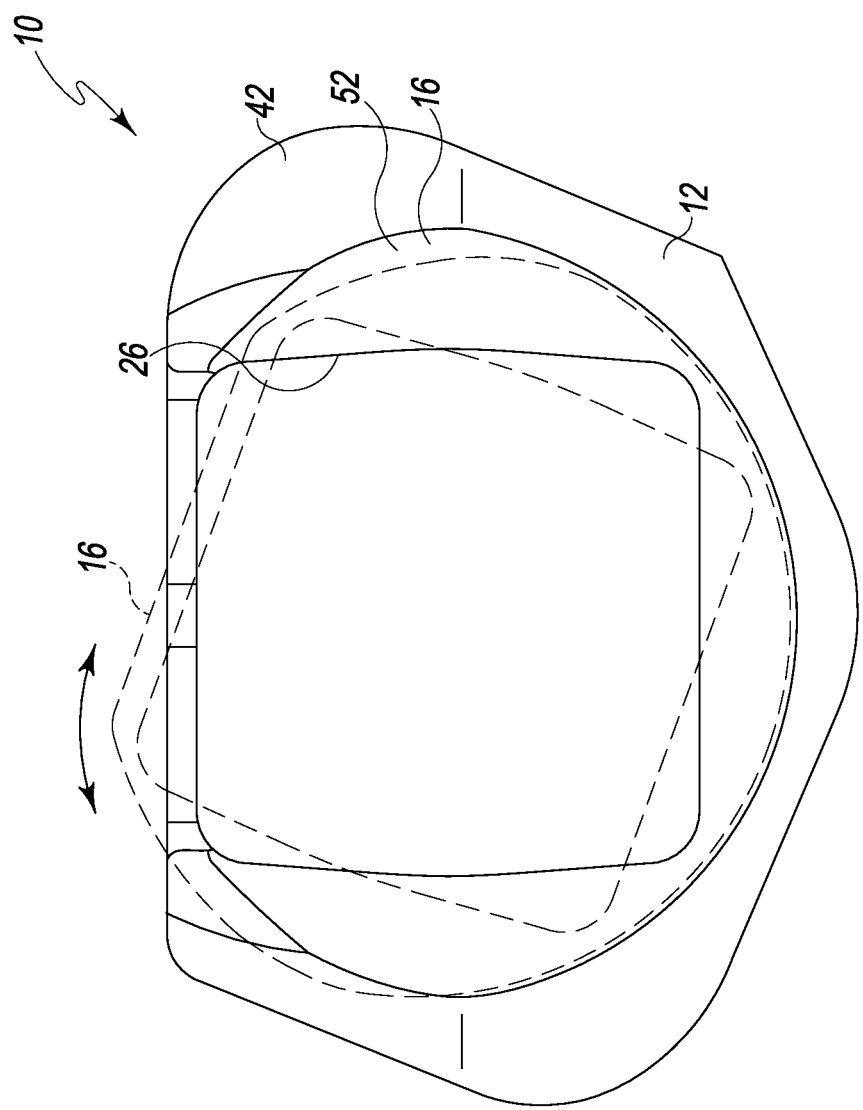
FIG. 10 is an inferior view showing rotation of the bearing insert relative to the tibial component.

Once the bearing insert 16 has been locked to the tibial component 12 in such a manner, it is constrained from linear movement relative to the tibial component 12. In particular, the size and configuration of the pedestal 54 closely conforms to the size and configuration of the annular sidewall 30 of the tibial component's platform 22 such that linear movement of the bearing insert 16 relative to the tibial component 12 in the anterior/posterior, medial/lateral, or superior/inferior directions is resisted. However, as shown in FIG. 10, the bearing insert 16 is rotative relative to the tibial component 12. Specifically, the retaining flange 58 and the distal end 62 of the locking tab 60 are freely movable along the annular sidewall 30 of the tibial component's platform 22 (i.e., within the undercut 38) thereby allowing the pedestal (and hence the bearing insert 16) to rotate freely relative to the tibial component 12.

Such rotation of the bearing insert 16 relative to the tibial component 12 allows the ankle prosthesis 10 to more closely mimic the kinematics of a natural ankle relative to other semi-constrained ankle prostheses. In particular, in addition to extension and flexion, the ankle prosthesis 10 allows for an extended range of motion of inversion and eversion relative to other semi-constrained ankle prostheses.

In addition, as shown in FIGS. 11 and 12, rotation of the bearing insert 16 relative to the tibial component 12 may facilitate the reduction of clinical implications of misalignment of the articulating components of an ankle prosthesis—namely, polymer wear, impingement of components, and cold flow—relative to other semi-constrained ankle prostheses. Specifically, rotation of the bearing insert 16 relative to the tibial component 12 allows radii congruency between the bearing insert 16 and the talar component 14 to be maintained even in the absence of optimal implant positioning.

As described above, the retaining flange 58 and the locking tab 60 prevent unintended migration of the bearing insert 16 away from the tibial component 12 (e.g., prevents lift-off of the bearing insert 16 from the tibial component 12). As can be seen best in FIGS. 8 and 9, the locking tab 60 is wider than the slot 46 formed in the anterior sidewall 44 of the tibial component 12. As such, the locking tab 60 is prevented from escaping the undercut 38 through the slot 46. Because of this, the locking tab 60 is maintained in the undercut 38 throughout rotation of the bearing insert 16.

However, a surgeon or other user may selectively engage the locking tab 60 to unlock and thereafter remove the bearing insert 16 from the tibial component 12. Specifically, the surgeon may advance the tip of an elongated surgical instrument or the like (not shown) through the slot 46 formed in the anterior sidewall 44 of the tibial component 12 to engage the locking tab 60 of the bearing insert 16. The surgeon may then push the locking tab 60 posteriorly such that the anterior edge 66 of the locking tab's angled surface 64 clears the inferior surface 32 of the tibial component's platform 22 thereby allowing the anterior side of the bearing insert's pedestal 54 to be moved inferiorly. Thereafter, the bearing insert 16 may be urged anteriorly such that the retaining flange 58 is removed from tibial component's undercut 38 thereby freeing the bearing insert 16 from the tibial component 12.

The components of the ankle prosthesis 10 that engage the natural bone, such as the tibial component 12 and the talar component 14, may be constructed with a biocompatible metal, such as a cobalt chrome alloy, although other materials, such as ceramics, may also be used. The bone engaging surfaces of these components may be textured to facilitate cementing the component to the bone. Such surfaces may also be porous coated to promote bone ingrowth for permanent fixation. Moreover, the metal surfaces of the tibial component 12 that contact the bearing insert 16 may be polished. For example, the inferior surface 32 and the bottom surface 36 of the tibial component 12 contact the superior surface 56 and the superior-most surface of the pedestal 54 of the bearing insert 16, respectively. Both of these metal surfaces of the tibial component 12 may be polished to facilitate rotation of the bearing insert 16 relative to the tibial component 12.

The bearing insert 16 may be constructed with a material that allows for smooth articulation between the bearing insert 16 and the talar component 14, such as a polymeric material. One such polymeric material is polyethylene such as ultra-high molecular weight polyethylene (UHMWPE), although numerous other types of biocompatible polymers may also be used.

It should be appreciated that the locking mechanism described herein is exemplary in nature, and that other configurations of locking mechanisms may be used to fit the needs of a given design of an ankle prosthesis. For example, other embodiments of snap-locking mechanisms may be used to lock the bearing insert to the tibial component in lieu of the tab 60. Such alternative embodiments may include a single locking tab located in a different location or possessing a different geometry, or they may include multiple locking tabs. Moreover, the position of the pedestal and the recess may be reversed with a pedestal extending inferiorly from the tibial component that is received into a recess formed in the bearing insert. Such an inverted design may likewise include a different embodiment of a locking mechanism other than the locking tab 60 and its associated components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. A semi-constrained ankle prosthesis, comprising:
a tibial component configured to be coupled to a surgically-prepared surface of the distal end of a tibia, the tibial component including (i) an annular sidewall that defines a recess and has an undercut formed therein and (ii) an outer sidewall that has an opening defined therein that opens into the recess,
a polymeric bearing insert having an articular surface formed in an inferior surface thereof, the bearing insert being locked to the tibial component and rotative relative thereto and including (i) a single locking tab having a body and a flange extending anteriorly from the body and (ii) one and only one retaining flange that extends posteriorly when the bearing insert is in a first position, the retaining flange being positioned on only a portion of a posterior side of the polymeric bearing insert and positioned in a posterior section of the undercut formed in the annular sidewall when the bearing insert is in the first position, and
a talar component configured to be coupled to a surgically-prepared surface of the proximal end of a talus, the talar component having an articular surface that is configured to articulate with the articular surface of the bearing insert,
wherein the flange of the locking tab is wider than the opening formed in the outer sidewall of the tibial component and includes an inferior edge that is positioned in an anterior section of the undercut formed in the annular sidewall when the bearing insert is in the first position.

2. The semi-constrained ankle prosthesis of claim 1, wherein:
the bearing insert comprises a superiorly extending pedestal that is positioned in the recess.

3. The semi-constrained ankle prosthesis of claim 2, wherein the retaining flange is located on the posterior side of the pedestal and the locking tab is located on the anterior side of the pedestal.

4. The semi-constrained ankle prosthesis of claim 2, wherein:
the outer sidewall extends from a superior surface of the tibial component to an inferior surface of the tibial component.

5. The semi-constrained ankle prosthesis of claim 1, wherein the tibial component comprises a polished metal inferior surface positioned in contact with a superior surface of the bearing insert.

6. A semi-constrained ankle prosthesis, comprising:
a talar component configured to be coupled to a surgically-prepared surface of the proximal end of a talus, the talar component having an articular surface,
a tibial component configured to be coupled to a surgically-prepared surface of the distal end of a tibia, the tibial component comprising a platform having (i) an annular sidewall that defines a recess, the annular sidewall having an undercut formed therein, (ii) an anterior sidewall that extends from a superior surface of the platform to an inferior surface of the platform, the anterior sidewall having an opening that extends superiorly from the inferior surface and opens into the recess, and
a bearing insert rotatable between a plurality of positions relative to the tibial component, the bearing insert comprising (i) a base having an articular surface formed in an inferior surface thereof, the articular surface of the bearing insert being configured to articulate with the articular surface of the talar component, (ii) a pedestal extending superiorly from a superior surface of the base, the pedestal being positioned in the recess of the tibial component so as to lock the bearing insert to the tibial component and permit the bearing insert to rotate relative to the tibial component, and (iii) one and only one retaining flange extending from the pedestal, the retaining flange extending posteriorly from the pedestal along only a portion of a posterior side of the pedestal and being positioned in a posterior section of the undercut when the bearing insert is in a first position of the plurality of positions,
wherein the pedestal includes a single locking tab having (i) a body extending superiorly from the base of the bearing insert and (ii) a flange extending anteriorly from the body, the flange being wider than the opening formed in the anterior sidewall of the platform and having an inferior edge positioned in an anterior section of the undercut when the bearing insert is in the first position.

7. The semi-constrained ankle prosthesis of claim 6, wherein the locking tab is located on the anterior side of the pedestal.

8. The semi-constrained ankle prosthesis of claim 6, wherein:
the platform of the tibial component comprises (i) an inferior surface positioned in contact with the superior surface of the bearing insert, and (ii) a bottom surface that is parallel to, and spaced apart superiorly from, the inferior surface, the bottom surface defining the bottom of the recess, and both the inferior surface and the bottom surface comprise polished metal surfaces.

9. A semi-constrained ankle prosthesis, comprising:

a tibial component configured to be coupled to a surgically-prepared surface of the distal end of a tibia, the tibial component including (i) an annular sidewall that defines a recess and has an undercut formed therein, and (ii) an anterior sidewall that has an opening defined therein that opens into the recess, a bearing insert snapped-locked to the tibial component, the bearing insert being rotative relative to the tibial component between a plurality of positions and having an articular surface formed in an inferior surface thereof and including (i) a single locking tab located on the anterior side of the bearing insert, the locking tab having a body and a flange extending anteriorly from the body, (ii) a superiorly extending pedestal that is positioned in the recess, and (iii) one and only one retaining flange extending from the pedestal, the retaining flange extending posteriorly away from the pedestal, and a talar component configured to be coupled to a surgically-prepared surface of the proximal end of a talus, the talar component having an articular surface that is configured to articulate with the articular surface of the bearing insert, wherein (i) the flange of the locking tab is wider than the opening formed in the anterior sidewall of the tibial component and includes an inferior edge that is positioned in an anterior section of the undercut formed in the annular sidewall when the bearing insert is in a first position of the plurality of positions, and (ii) the retaining flange extends along only a posterior side of the pedestal and is positioned in a posterior section of the undercut when the bearing insert is in the first position.

10. The semi-constrained ankle prosthesis of claim 9, wherein:

the tibial component is metallic, and the bearing insert is polymeric.

11. The semi-constrained ankle prosthesis of claim 9, wherein:

the anterior sidewall extends from a superior surface of the tibial component to an inferior surface of the tibial component.

12. The semi-constrained ankle prosthesis of claim 9, wherein the tibial component comprises a polished metal inferior surface positioned in contact with a superior surface of the bearing insert.

* * * * *